US011000200B2

(12) United States Patent
Lee et al.

(10) Patent No.: US 11,000,200 B2
(45) Date of Patent: *May 11, 2021

(54) SYSTEMS AND METHODS FOR PEDAL REVASCULARIZATION ASSESSMENT

(71) Applicant: Pedra Technology Pte Ltd, Singapore (SG)

(72) Inventors: Kijoon Lee, Singapore (SG); Jing Dong, Singapore (SG); Renzhe Bi, Singapore (SG)

(73) Assignee: Pedra Technology PTE LTD, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/283,521

(22) Filed: Feb. 22, 2019

(65) Prior Publication Data

US 2020/0022595 A1 Jan. 23, 2020

Related U.S. Application Data

(63) Continuation of application No. 15/583,746, filed on May 1, 2017, now Pat. No. 10,213,122, which is a continuation of application No. 13/967,298, filed on Aug. 14, 2013, now Pat. No. 9,636,025.

(60) Provisional application No. 61/683,704, filed on Aug. 15, 2012, provisional application No. 61/830,499, filed on Jun. 3, 2013.

(51) Int. Cl.
*A61B 5/026* (2006.01)
*A61B 5/00* (2006.01)

(52) U.S. Cl.
CPC .......... *A61B 5/0261* (2013.01); *A61B 5/0059* (2013.01); *A61B 5/683* (2013.01); *A61B 5/6825* (2013.01); *A61B 5/6829* (2013.01); *A61B 5/6831* (2013.01); *A61B 5/7278* (2013.01); *A61B 5/74* (2013.01); *A61B 5/742* (2013.01); *A61B 5/7405* (2013.01); *A61B 5/7455* (2013.01)

(58) Field of Classification Search
None
See application file for complete search history.

(56) References Cited

U.S. PATENT DOCUMENTS

| | | | |
|---|---|---|---|
| 4,050,450 | A | 9/1977 | Polanyi et al. |
| 5,991,697 | A | 11/1999 | Nelson et al. |
| 6,076,010 | A | 6/2000 | Boas et al. |
| 6,388,240 | B2 | 5/2002 | Schulz et al. |

(Continued)

*Primary Examiner* — Carolyn A Pehlke
(74) *Attorney, Agent, or Firm* — Knobbe Martens Olson & Bear, LLP

(57) ABSTRACT

Diffuse optical flow (DOF) sensors can be used to assess deep tissue flow. DOF sensors positioned on a foot can provide fluctuating light intensity data to an analyzer, which can then determine absolute and/or relative blood flow. The determined absolute and/or relative blood flow can be signaled to an operator, for example a surgeon for intraoperative use. DOF sensors may be utilized to assess pedal revascularization, for example to guide interventional procedures and to evaluate their efficacy. A support structure can carry a plurality of DOF sensors, such that when the support structure is placed onto a patient's foot, the DOF sensors are disposed adjacent different locations on the foot. The different locations may correspond to different topographical regions of the foot, for example different pedal angiosomes.

15 Claims, 16 Drawing Sheets

(56) References Cited

U.S. PATENT DOCUMENTS

| | | |
|---|---|---|
| 6,546,267 B1 | 4/2003 | Sugiura et al. |
| 6,549,284 B1 | 4/2003 | Boas et al. |
| 7,043,287 B1 | 5/2006 | Khalil et al. |
| 7,113,817 B1 | 9/2006 | Winchester, Jr. et al. |
| 7,460,900 B1 | 12/2008 | Gill et al. |
| 8,082,015 B2 | 12/2011 | Yodh et al. |
| 8,480,579 B2 | 7/2013 | Serov et al. |
| 8,666,468 B1 | 3/2014 | Al-Ali |
| 8,965,473 B2 | 2/2015 | Hoarau et al. |
| 9,636,025 B2 | 5/2017 | Lee et al. |
| 10,213,122 B2 | 2/2019 | Lee et al. |
| 2002/0180972 A1 | 12/2002 | Ansari et al. |
| 2004/0243006 A1 | 12/2004 | Nakata et al. |
| 2006/0063995 A1 | 3/2006 | Yodh et al. |
| 2007/0179366 A1 | 8/2007 | Pewzner et al. |
| 2007/0208404 A1 | 9/2007 | Jones et al. |
| 2008/0082135 A1 | 4/2008 | Arcot-Krishnamurthy et al. |
| 2008/0287808 A1 | 11/2008 | Tearney et al. |
| 2009/0091741 A1 | 4/2009 | Dogariu |
| 2009/0149764 A1 | 6/2009 | Semler et al. |
| 2009/0177107 A1 | 7/2009 | Guion-Johnson |
| 2009/0287076 A1 | 11/2009 | Boyden et al. |
| 2010/0016733 A1 | 1/2010 | Smith et al. |
| 2010/0056928 A1 | 3/2010 | Zuzak et al. |
| 2010/0210931 A1 | 8/2010 | Cuccia et al. |
| 2011/0013002 A1 | 1/2011 | Thompson et al. |
| 2011/0128555 A1 | 6/2011 | Rotschild et al. |
| 2012/0071769 A1 | 3/2012 | Dunn et al. |
| 2012/0095354 A1 | 4/2012 | Dunn et al. |
| 2012/0130215 A1 | 5/2012 | Fine et al. |
| 2012/0184831 A1 | 7/2012 | Seetamraju et al. |
| 2012/0188354 A1* | 7/2012 | Munro ............ H04N 5/332 348/77 |
| 2012/0245439 A1 | 9/2012 | Andre et al. |
| 2014/0052006 A1 | 2/2014 | Lee et al. |
| 2014/0094666 A1* | 4/2014 | Fine ............ A61B 5/7246 600/316 |
| 2014/0111671 A1 | 4/2014 | Cao et al. |
| 2014/0206980 A1 | 7/2014 | Lee et al. |
| 2015/0073271 A1 | 3/2015 | Lee et al. |
| 2017/0231510 A1 | 8/2017 | Lee et al. |
| 2017/0311819 A1 | 11/2017 | Lee et al. |
| 2018/0368705 A1 | 12/2018 | Lee et al. |

* cited by examiner

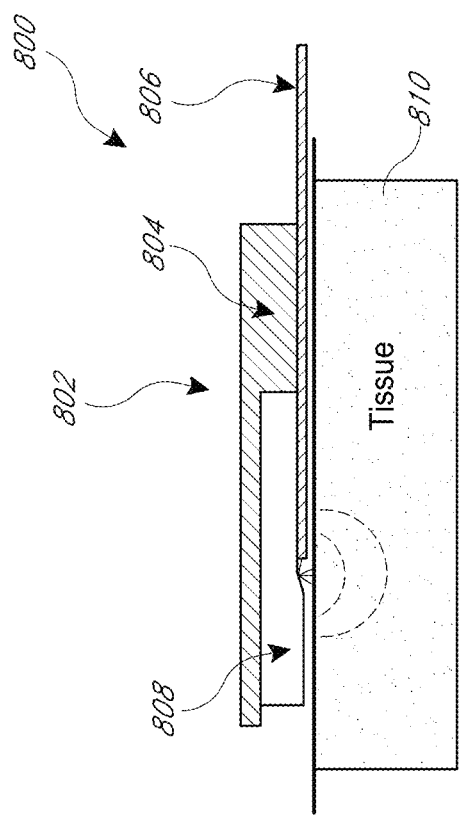
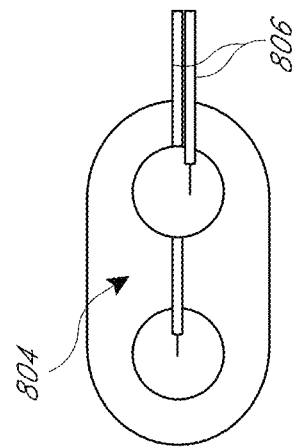
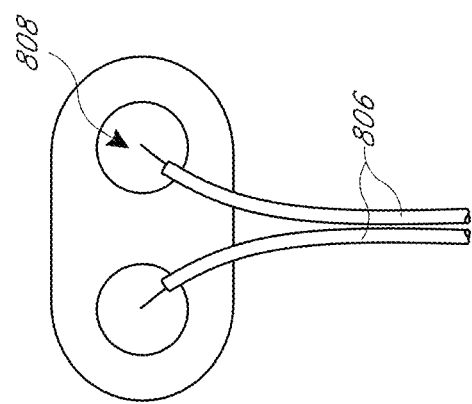
FIG. 8A
FIG. 8C
FIG. 8B

SYSTEMS AND METHODS FOR PEDAL REVASCULARIZATION ASSESSMENT

CROSS-REFERENCE TO RELATED APPLICATIONS

This application is a continuation of U.S. application Ser. No. 15/583,746 filed on May 1, 2017, which is a continuation of Ser. No. 13/967,298 filed on Aug. 14, 2013, which claims the benefit as a nonprovisional of U.S. Provisional App. No. 61/683,704, filed on Aug. 15, 2012, and 61/830,499, filed Jun. 3, 2013. Each of these foregoing applications is hereby incorporated by reference in its entirety.

BACKGROUND OF THE INVENTION

Field of the Invention

This disclosure relates to the measurement of blood flow in tissue, in particular measurement of blood flow in the foot.

Description of the Related Art

Peripheral arterial disease (PAD) is a progressive disease in which narrowed or obstructed arteries reduce blood flow to the limbs. PAD can result from atherosclerosis, inflammatory processes leading to stenosis, an embolism, or thrombus formation, and is associated with smoking, diabetes, dyslipidemia, and hypertension. PAD can if untreated result in critical limb ischemia (CLI), in which blood flow to the limb (usually the legs and feet) is compromised to such an extent that tissue damage ensues with consequent ulceration, gangrene or loss of the limb. Patients with PAD are also at a disproportionately high risk of other cardiovascular diseases like myocardial infarction and stroke and of death as a result of these conditions. With the incidence of diabetes increasing worldwide, treatment of CLI and prevention of disability and of limb loss from it has become a significant health priority.

Peripheral vascular intervention procedures using endovascular (minimally invasive) intervention, open surgery or a combination of the two are currently the only methods available to restore perfusion to the limbs in patients with PAD. Medical management can help only to delay the progression of the disease, if at all. However, clinicians currently lack the intraoperative tools to properly assess perfusion in the affected tissue, usually in the feet, in real-time to reliably guide the conduct of the interventional procedure. Existing technologies that measure blood perfusion include skin perfusion pressure (SPP), duplex ultrasound (DUX), and transcutaneous oxygen monitoring (TCOM). Each of these techniques suffers from one or more disadvantages. SPP only provides perfusion data at the skin dermis level, requires the skin temperature to be normalized to 44° C., is affected by skin pigmentation and is unreliable with patients with edema. SPP also requires the use of a pressure cuff, which further limits its utility as a real-time perfusion assessment tool during peripheral vascular interventions. DUX does not assess tissue perfusion but instead measures blood flow in large vessels (>1.5 mm). TCOM requires the patient to be placed on hyperbaric oxygen, making it incompatible with the cath lab/operating room. Furthermore, TCOM does not provide real time revascularization data as it takes about 4 to 6 weeks for the measurements to equilibrate.

Accordingly, there is a need for noninvasive, real-time measurement of blood perfusion in a range of blood vessel sizes and in the tissue supplied by these vessels. In particular, there is a need for noninvasive, real-time measurement of blood perfusion in the foot that can be reliably performed as the interventional procedure proceeds and be used to inform the decision making during the procedure.

SUMMARY OF THE INVENTION

Disclosed herein is a system for assessment of peripheral blood flow during peripheral vascular intervention, the system including: a support structure configured to be positioned onto a patient's foot; a diffuse optical flow (DOF) sensor carried by the support structure; an analyzer configured to analyze data from the DOF sensor to determine absolute and/or relative blood flow at a location near the DOF sensor when the support structure is positioned onto a patient's foot; and a feedback device configured to provide a signal indicative of the absolute and/or relative blood flow determined by the analyzer.

In some embodiments, the support structure can include a retention ring and an adhesive material. In some embodiments, the support structure can include a strap having the DOF sensor attached thereto. In some embodiments, the DOF sensors can be arranged such that when the support structure is positioned onto the patient's foot, at least two of the DOF sensors are over different topographical locations in the foot including different pedal angiosomes. In some embodiments, the DOF sensors can be arranged such that when the support structure is positioned onto the patient's foot, at least five of the DOF sensors are over different topographical locations in the foot including different pedal angiosomes. In some embodiments, the analyzer can include a software autocorrelator. In some embodiments, the analyzer can include a hardware autocorrelator. In some embodiments, the signal indicative of the absolute and/or relative blood flow can be visual, audible, or tactile. In some embodiments, the system can be configured to provide the signal indicative of the absolute and/or relative blood flow in substantially real-time. In some embodiments, the system can be configured to provide the signal indicative of the absolute and/or relative blood flow within 1 second from measurement.

Also disclosed herein is a method for real-time assessment of peripheral blood flow during peripheral vascular intervention procedures, the method including: disposing at least one diffuse optical flow (DOF) sensor adjacent to a location on a foot of a patient; obtaining measurements of intensity fluctuation from the DOF sensor; analyzing the obtained measurements to determine an absolute and/or relative blood flow rate at the location; and signaling the determined absolute and/or relative blood flow rate to an operator.

In some embodiments, disposing the at least one DOF sensor can include placing a support structure onto the foot of the patient, the DOF sensor being carried by the support structure. In some embodiments, the method can further comprise disposing a plurality of DOF sensors adjacent to a respective plurality of locations on the foot of the patient. In some embodiments, the plurality of locations can include at least two locations corresponding to different topographical locations in the foot including different pedal angiosomes. In some embodiments, plurality of locations can include at least five locations corresponding to five different topographical locations in the foot including different pedal angiosomes. In some embodiments, signaling can include providing visual, audible, or tactile indicia of absolute and/or relative blood flow. In some embodiments, signaling the determined absolute and/or relative blood flow rate to an operator can be performed in less than 1 second from measurement.

Further disclosed is a method for assessment of peripheral blood flow during peripheral vascular intervention procedures, the method including: disposing a plurality of diffuse optical flow (DOF) sensors adjacent to a respective plurality of locations on an extremity of a patient, wherein at least two of the locations correspond to different topographical locations in the foot including different pedal angiosomes; determining an absolute and/or relative blood flow rates at each of the plurality of locations in the extremity of the patient; and signaling the determined absolute and/or relative blood flow rates to an operator.

In some embodiments, the extremity can be a foot. In some embodiments, the extremity can be a hand. In some embodiments, the signaling can be performed in substantially real-time. In some embodiments, the determined absolute and/or relative blood flow rates can be utilized to assess the efficacy of an interventional procedure.

Also disclosed herein is a patient interface, for supporting a plurality of diffuse optical flow (DOF) sensors in optical communication with a patient's foot, comprising: a support, configured to be mountable on and carried by the foot; at least three sensors carried by the support, each sensor corresponding to a separate topographical location in the foot including an angiosome selected from the group consisting of: the angiosome of the medial plantar artery; the angiosome of the lateral plantar artery; the angiosome of the calcaneal branch of the posterior tibial artery; the angiosome of the calcaneal branch of the peroneal artery; and the angiosome of the dorsalis pedis artery.

In some embodiments, the patient interface can include at least four sensors carried by the support, each sensor corresponding to a separate topographical location in the foot including a pedal angiosome. In some embodiments, the support can comprise a retention ring and adhesive material. In some embodiments, the support can comprise an optical source fiber and an optical detector fiber. In some embodiments, the optical source fiber and the optical detector fiber can further comprise at least one coupling for releasably coupling the sensor to an analyzer. In some embodiments, the patient interface can comprise a cable, which includes a plurality of pairs of source fibers and detector fibers, each pair connected to a separate sensor. In some embodiments, each sensor can be releasably carried by the support.

Also disclosed herein is a system for assessment of peripheral blood perfusion, the system including: a support structure configured to be positioned onto a patient's foot; a diffuse optical sensor carried by the support structure; an analyzer configured to analyze data from the diffuse optical sensor to characterize the composition or flow of blood at a location near the diffuse optical sensor when the support structure is positioned ontPEDRAo a patient's foot; and a feedback device configured to provide a signal indicative of composition or flow of blood determined by the analyzer.

Further disclosed herein is a method for real-time assessment of peripheral blood, the method including: disposing at least one diffuse optical sensor adjacent to a location on a foot of a patient; obtaining measurements of diffused light; analyzing the obtained measurements to characterize the composition and/or flow rate of blood at the location; and signaling the determined composition and/or flow rate to an operator.

Also disclosed is a method for assessment of peripheral blood flow during peripheral vascular intervention procedures, the method including: disposing a plurality of diffuse optical sensors adjacent to a respective plurality of locations on an extremity of a patient, wherein at least two of the locations correspond to different topographical locations in the foot including different pedal angiosomes; characterizing the composition and/or blood flow rates at each of the plurality of locations in the extremity of the patient; and signaling the composition and/or blood flow rates to an operator.

Further disclosed herein is a patient interface, for supporting a plurality of diffuse optical sensors in optical communication with a patient's foot, comprising: a support, configured to be mountable on and carried by the foot; at least three sensors carried by the support, each sensor corresponding to a separate topographical location in the foot including angiosome selected from the group consisting of: the angiosome of the medial plantar artery; the angiosome of the lateral plantar artery; the angiosome of the calcaneal branch of the posterior tibial artery; the angiosome of the calcaneal branch of the peroneal artery; and the angiosome of the dorsalis pedis artery.

BRIEF DESCRIPTION OF THE DRAWINGS

FIGS. 8A-8C illustrate an embodiment of a DOF sensor, with a horizontal sensor head.

DETAILED DESCRIPTION OF THE PREFERRED EMBODIMENT

Figure 1B:
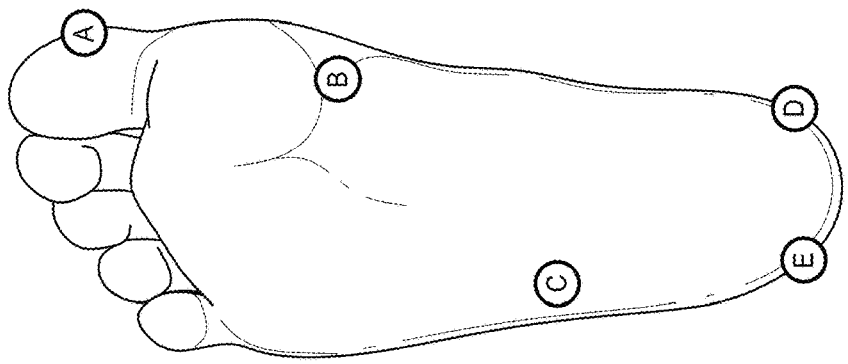
FIG. 1B illustrates five measurement points on the foot, each corresponding to one of the angiosomes shown in FIG. 1A.

A number of techniques exist for characterizing blood flow, relying on measuring of diffusion of light. Such techniques include Diffuse Correlation Spectroscopy (DCS) and Diffuse Speckle Contrast Analysis (DSCA). Both DCS and DSCA can be used to measure relative and/or absolute blood flow. Other techniques rely on measuring diffusion of light to detect other characteristics of tissue, such as biochemical composition, concentrations of oxyhemoglobin and deoxyhemoglobin, etc. Such techniques include Diffuse Optical Spectroscopy (DOS), Diffuse Optical Tomography (DOT), and Near-Infrared Spectroscopy (NIRS).

As used herein, "diffuse optical sensor" includes any sensor configured to characterize properties of blood in tissue via measurement of diffuse light. As such, diffuse optical sensors include DCS, DSCA, DOS, DOT, and NIRS sensors. As used herein, the term "diffuse optical flow sensor" includes any sensor configured to characterize blood flow in tissue. As such, diffuse optical flow (DOF) sensors include both DCS and DSCA sensors.

Near-infrared diffuse correlation spectroscopy (DCS) is an emerging technique for continuous noninvasive measurement of blood flow in biological tissues. In the last decade or so, DCS technology has been developed to noninvasively sense the blood flow information in deep tissue vasculature such as brain, muscle, and breast. In contrast to some other blood flow measurement techniques, such as positron emission tomography (PET), single photon emission computed tomography (SPECT), and xenon-enhanced computed tomography (XeCT), DCS uses non-ionizing radiation and requires no contrast agents. It does not interfere with commonly used medical devices such as pacemakers and metal implants. It therefore has potential in cancer therapy monitoring and bedside monitoring in clinical settings.

A DCS system can include a light source such as a laser with a long coherence length, a detector such as a photon-counting avalanche photodiode (APD) or photomultiplier tube (PMT), and an autocorrelator. In various embodiments, the autocorrelator may take the form of hardware or software. As one of the central components of the DCS system, the autocorrelator computes the autocorrelation function of the temporal fluctuation of the light intensity obtained from the detector.

However, DCS can suffer from a long integration time, high cost, and low channel number of simultaneous measurements. One factor contributing to these limitations is dependence on very sensitive photodetector(s) and subsequent autocorrelation calculation. Diffuse Speckle Contrast Analysis (DSCA) is a newer technology that provides an improved flowmetry system enabling cost-effective, real-time measurements using statistical analysis without having to rely on autocorrelation analysis on fast time-series data. This statistical analysis can be implemented either in spatial domain using a multi-pixel image sensor, or in the time domain using slow counter. A multi-pixel image sensor can also be used for time domain analysis such that single or multiple pixels act as an individual detector, which is especially suitable for multi-channel application. In various embodiments, this approach can be used to measure blood flow, whether absolute, relative, or both.

DSCA can be implemented in both spatial and time domains. For spatial DSCA (sDSCA), a raw speckle image is first obtained from the sample surface. The raw speckle images may first be normalized by the smooth intensity background, which can be averaged over a number of speckle images. The speckle contrast, $K_s$ is defined as the ratio of the standard deviation to the mean intensity across many detectors or pixels, $K_s=\sigma_s/<I>$, where subscript s refers to the spatial, as opposed to temporal, variations. The quantity $K_s$ is related to the field autocorrelation function $g_1(\tau)$ as follows:

$$V(T) = [K_s(T)]^2 = \frac{2}{T}\int_0^T (1-\tau/T)[g_1(\tau)]^2 d\tau$$

where V is the intensity variance across the image, and T is the image sensor exposure time. By using the known solution of the correlation diffusion equation in the semi-infinite medium, the formal relationship between the flow rate and $K_s$ can be derived. The relationship between the flow and $1/K_s^2$ turns out to be substantially linear in the range of flow seen in body tissue, with $1/K_s^2$ increasing with increasing flow rate.

Another way to implement this speckle contrast rationale for flowmetry is to use statistical analysis on time series data obtained by integrating over a certain time. This temporal domain analysis is referred to herein as tDSCA. The integrating time for tDSCA can be regarded as analogous to the exposure time of the image sensor in sDSCA. In the case of tDSCA, a detector with moderate sensitivity with an integrating circuit can be used. For example, each pixel on a CCD chip can be used for this purpose as each CCD pixel keeps accumulating photoelectrons for a given exposure time. Therefore, a number of single-mode fibers can be directly positioned on some locations on a single CCD chip, resulting in a multi-channel tDSCA system without losing any time resolution. The number of channels is only limited by the CCD chip size, pixel size, and the area of each fiber tip. In some embodiments, tDSCA can use sensitive detectors such as avalanche photodiode (APD) and/or photomultiplier tube (PMT) with a slow counter such as a counter included in a DAQ card with USB connection, but scaling this embodiment to multichannel instrument is costly and bulky. Time-series data taken either way can be obtained by repeat measurements, for example 25 measurements can be made consecutively, after which the data can be analyzed statistically to determine the flow rate. In a configuration with an exposure time of 1 ms, one flow index would be obtained every 25 ms, resulting in approximately 40 Hz operation.

The statistical analysis of the time-series data can be substantially identical to that described above with respect to sDSCA, except that the statistics (average intensity and standard deviation of intensity) are calculated in the time domain, rather than the spatial domain. As a result, tDSCA may provide lower time resolution than sDSCA. However, the detector area for tDSCA may be significantly smaller than with sDSCA. As with the spatial domain counterpart, tDSCA provides an approach with instrumentation and analysis that are significantly simpler and less computationally intensive than traditional DCS techniques.

Both DCS and DSCA technology can be used to evaluate on a real-time basis the absolute and/or relative blood flow in the foot, thereby providing an important tool for interventional radiologists and vascular surgeons treating ischemia in the foot. With current tools in the operating room, the physician can usually assess via X-ray fluoroscopy whether an intervention such as a balloon angioplasty procedure has succeeded in opening up and achieving patency of a limb artery. However, the clinical experience has been that structural patency as observed with fluoroscopy is not a reliable indicator of successful reperfusion of the topographical region of the foot where the ulcer wound, ischemic tissue (e.g. blackened toes) or other clinical manifestation is located. To augment fluoroscopic data on arterial patency, a plurality of DOF sensors used in either DCS or DSCA systems can be positioned at different topographical regions of the foot to assess absolute and/or relative blood flow in the different regions. For example, the topographical regions may correspond to different pedal angiosomes.

An angiosome is a three-dimensional portion of tissue supplied by an artery source and drained by its accompanying veins. It can include skin, fascia, muscle, or bone. Pedal angiosomes are illustrated in FIG. 1A. Below the knee, there are three main arteries: the anterior tibial artery, the posterior tibial artery, and the peroneal artery. The posterior tibial artery gives at least three separate branches: the calcaneal artery, the medial plantar artery, and lateral plantar artery, which each supply distinct portions of the foot. The anterior tibial artery supplies the anterior ankle and continues as the dorsalis pedis artery, which supplies much of the dorsum of the foot. The calcaneal branch of the peroneal artery supplies the lateral and plantar heel. The anterior perforating branch of the peroneal artery supplies the lateral anterior upper ankle. As a result, the pedal angiosomes include: the angiosome of the medial plantar artery, the angiosome of the lateral plantar artery, the angiosome of the calcaneal branch of the posterior tibial artery, the angiosome of the calcaneal branch of the peroneal artery, the angiosome of the dorsalis pedis artery. There is some debate as to whether there is a separate sixth pedal angiosome corresponding to the anterior perforating branch of the peroneal artery.

Figure 1A:
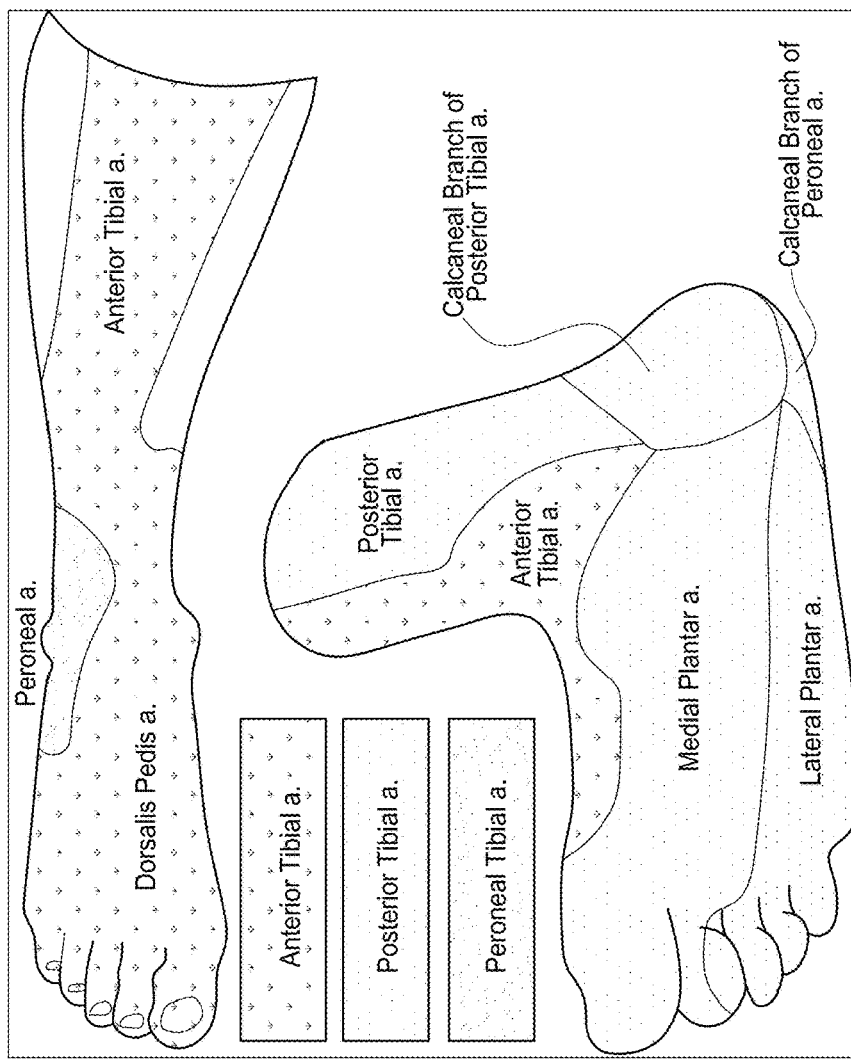
FIG. 1A illustrates the pedal angiosomes.

FIG. 1B illustrates five measurement points on the foot, each corresponding a pedal angiosome identified in FIG. 1A. By detecting blood flow in each of these positions, blood flow from the various arteries can be evaluated independently. For example, measurement of blood flow at point A (see FIG. 1D) is indicative of blood flow from the dorsalis pedis artery, and also the anterior tibial artery. Similarly, measurement of blood flow at point B (see FIG. 1E) corresponds to the medial plantar artery, while point C (see FIG. 1F) corresponds to the lateral plantar artery, point D (see FIG. 1G) corresponds to the calcaneal branch of the posterior tibial artery, and point E (see FIG. 1H) corresponds to the calcaneal branch of the peroneal artery.

Figure 1C:
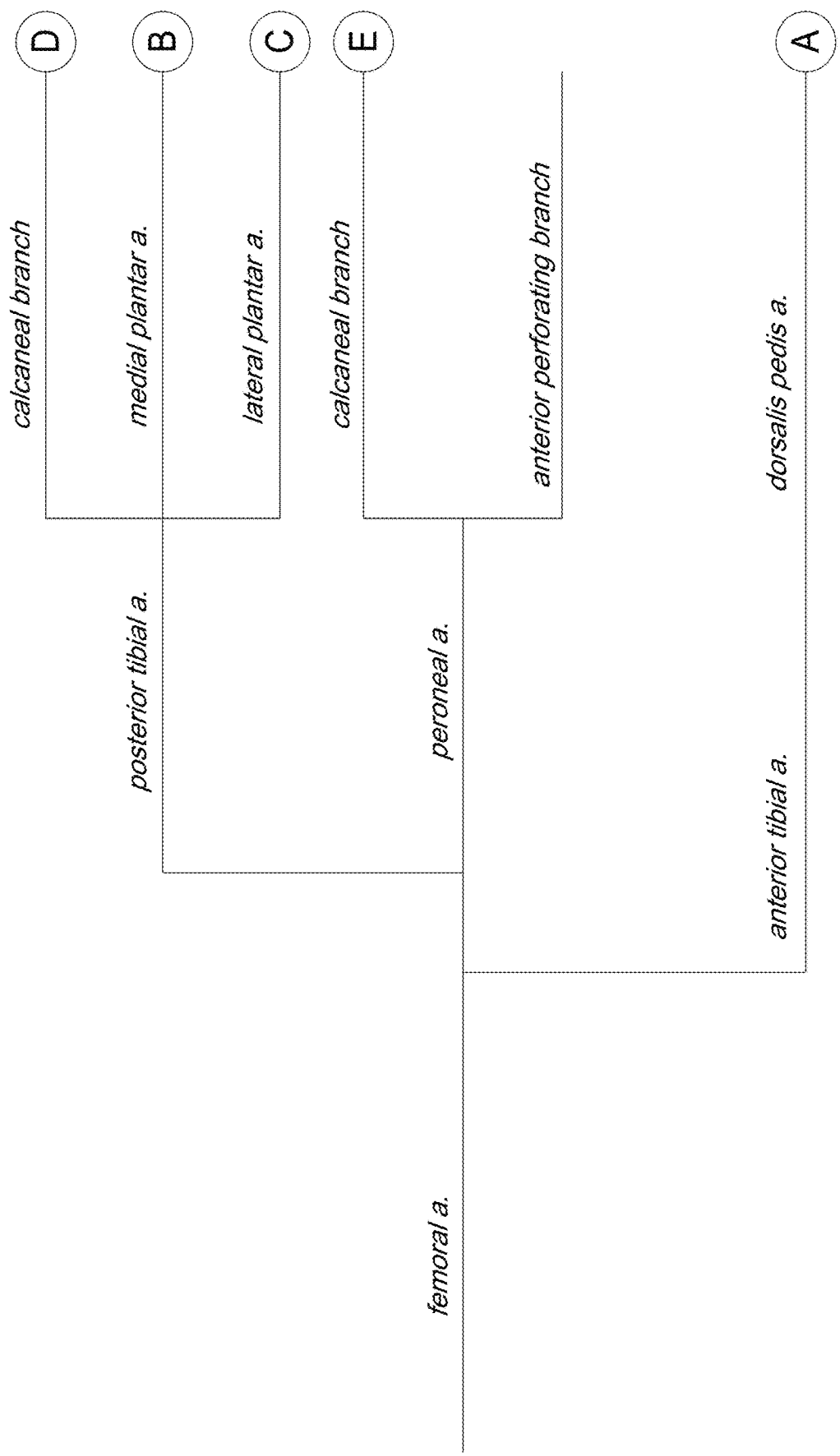
FIG. 1C illustrates the branching of the arteries supplying the pedal angiosomes.
Figure 1F:
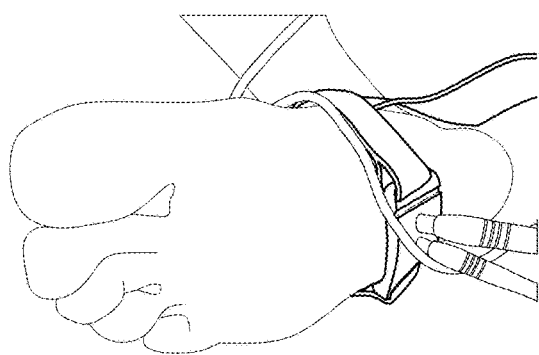
FIGS. 1D-1H illustrate measurement using diffuse optical flow (DOF) sensors at each of the five measurement positions of FIG. 1B.
Figure 1H:
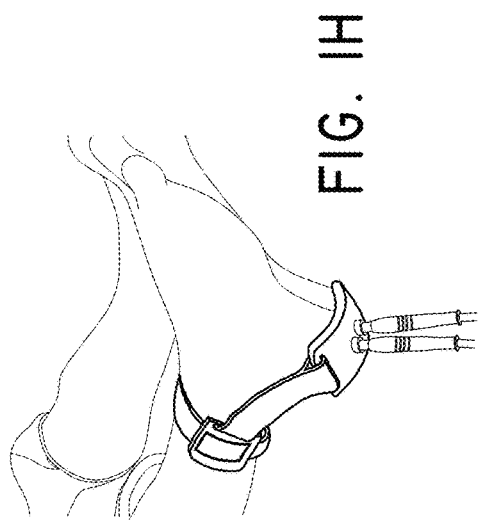
Figure 1E:
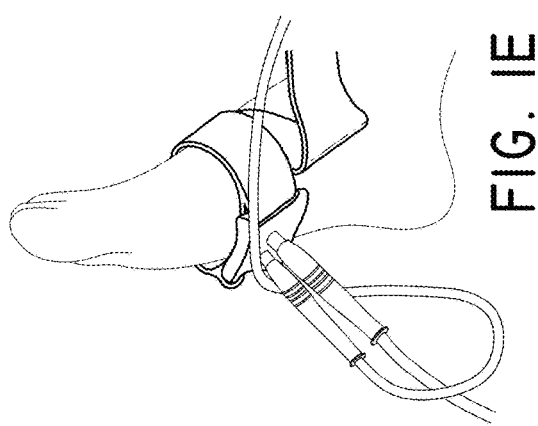
Figure 1D:
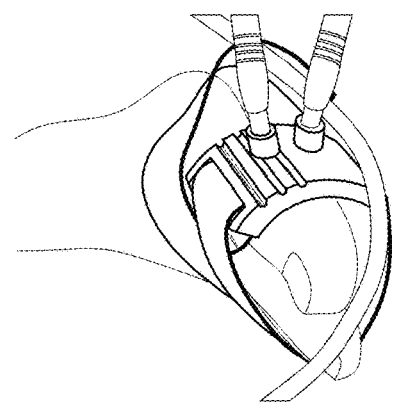
Figure 1G:
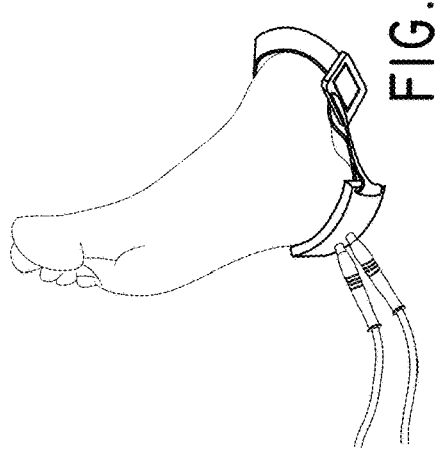

FIG. 1C is a branching diagram of the arteries supplying the pedal angiosomes. The blood flow measurement points A-E are illustrated as terminating respective artery branches, though in practice the measurement points need not be at the distal-most end of the respective arteries. As noted above, measurements at any of the points A-E may provide valuable clinical information regarding local perfusion.

Topographical-based peripheral vascular interventions, such as angiosome-directed peripheral vascular interventions, have been developed relatively recently, and show promising performance compared with traditional intervention, particularly in terms of improved limb salvage rates. A system employing a plurality of DOF sensors can provide real-time feedback on changes in perfusion of different topographical locations in the foot, e.g. angiosome by angiosome, so that interventional radiologists or vascular surgeons may immediately evaluate whether specific intervention at a target artery has succeeded in restoring sufficient blood perfusion to the targeted topographical region of the foot where the ulcer wound, ischemic tissue or other clinical manifestation is located. DCS or DSCA can also serve as tools to screen for peripheral arterial disease, by measuring blood flow in the extremities, for example in the foot.

Figure 2:
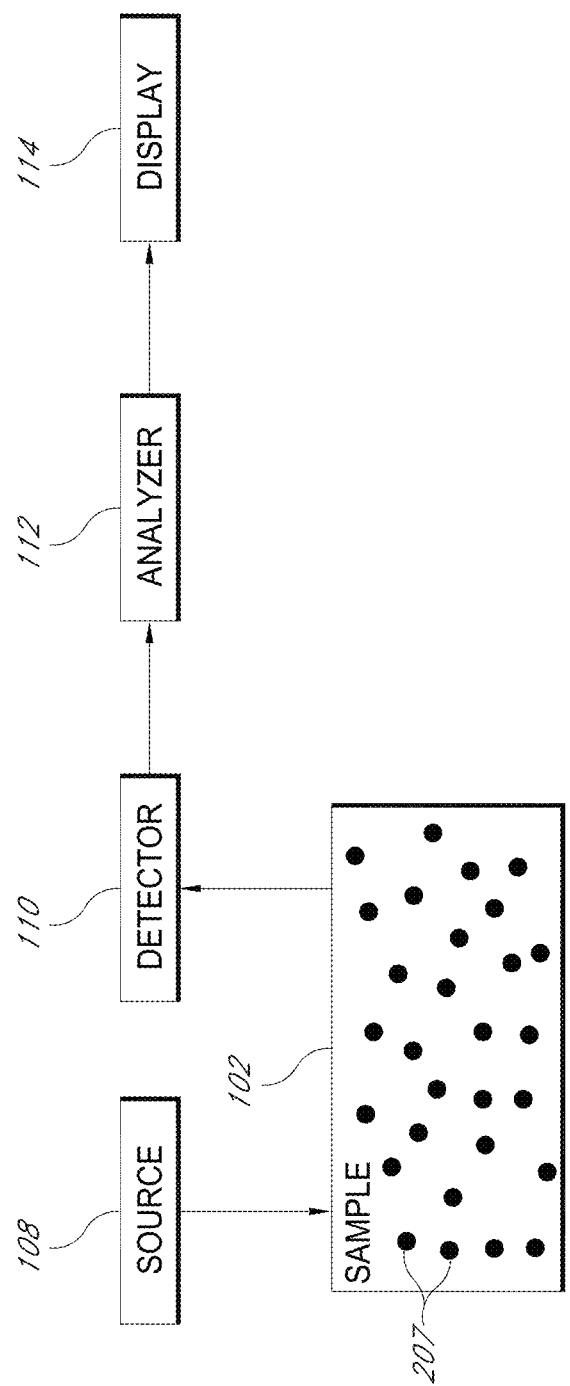
FIG. 2 is a block diagram of a system for measuring flow of turbid media.

FIG. 2 is a block diagram of a system for measuring flow of turbid media. A sample 102 includes a heterogeneous matrix therein. Within this matrix is an embedded flow layer with randomly ordered microcirculatory channels through which small particles 207 move in a non-ordered fashion. For example, in some embodiments the sample may be body tissue, with a complex network of peripheral arterioles and capillaries. A source 108 injects light into the sample 102. A detector 110 can detect light scattered by the moving particles 207 in the microcirculatory channels. The detector 110 can be positioned to receive light that passes from the source into the sample, and diffuses through the sample. In some embodiments, the detector can be coupled to the sample by a single-mode optical fiber. In some embodiments, the detector may be a multi-pixel image sensor, for example a CCD camera, used to image an area of the sample. In other embodiments, the detector may be a photon-counting avalanche photodiode (APD) or photomultiplier tube (PMT). As the particles flow in random direction, the scattering of light from the source 108 will vary, causing intensity fluctuations to be detected by the detector 110.

An analyzer 112 is coupled to detector 110 and configured to receive a signal from the detector 110. The analyzer 112 may comprise an autocorrelator, which measures the temporal intensity autocorrelation function of light received by the detector 110. The autocorrelation function can be used to obtain the scattering and flow characteristics of the small particles flowing in the sample 102. The time-dependent intensity fluctuations reflect the time-dependent density fluctuations of the small particles 207, and accordingly the autocorrelation function can be used to determine the flow rate within the sample 102. In some embodiments, a hardware autocorrelator may be employed, while in other embodiments a software autocorrelator can be used. The flow rate or other characteristic determined by the analyzer 112 may be output to a display 114. The measured quantity may therefore be provided to an operator via the display 114. In various embodiments, the operator may be a clinician, diagnostician, surgeon, surgical assistant, nurse, or other medical personnel. In some embodiments, the measurement may be provided via display 114 in substantially real-time. In some embodiments, the measurement may be provided via display 114 within about 1 second from measurement, i.e., within about 1 second of the time that the scattered light is detected by the detector, the measurement may be provided via display 114. In various embodiments, the measurement may be provided within less than about 10 minutes, within less than about 5 minutes, within less than about 1 minute, within less than about 30 seconds, within less than about 10 seconds, or within less than about 1 second from measurement.

In some embodiments, as noted above, a software autocorrelator may be used. This may advantageously provide additional flexibility compared with a hardware autocorrelator, as it allows for data pre-processing. A software autocorrelator may also reduce the cost of a DCS system, while also reducing size and improving form factor. The ability to pre-process data can also improve the accuracy of measurements.

Figure 3:
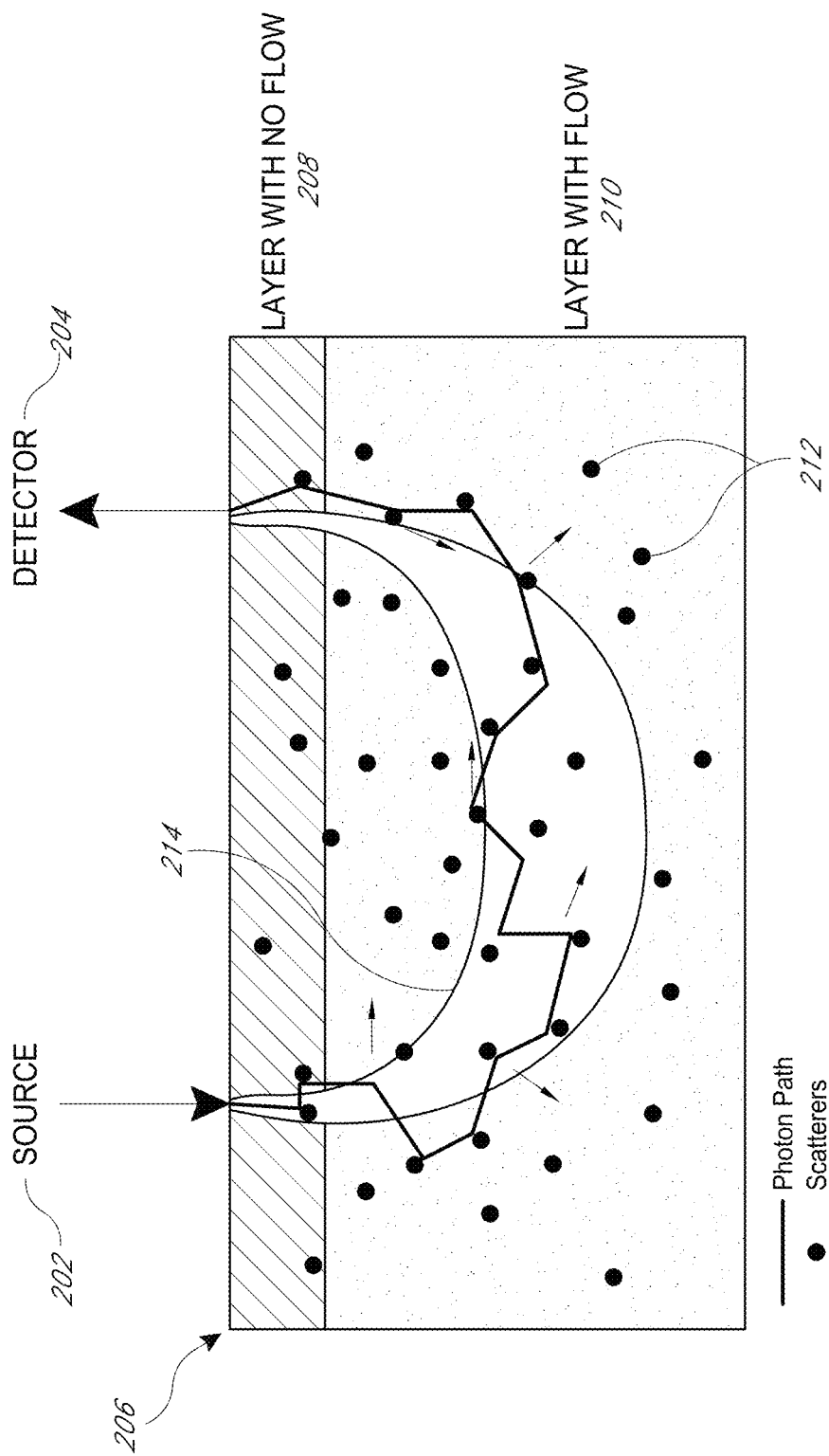
FIG. 3 is a schematic illustration of diffuse light penetration and detection in multi-layer tissue.
Figure 4:
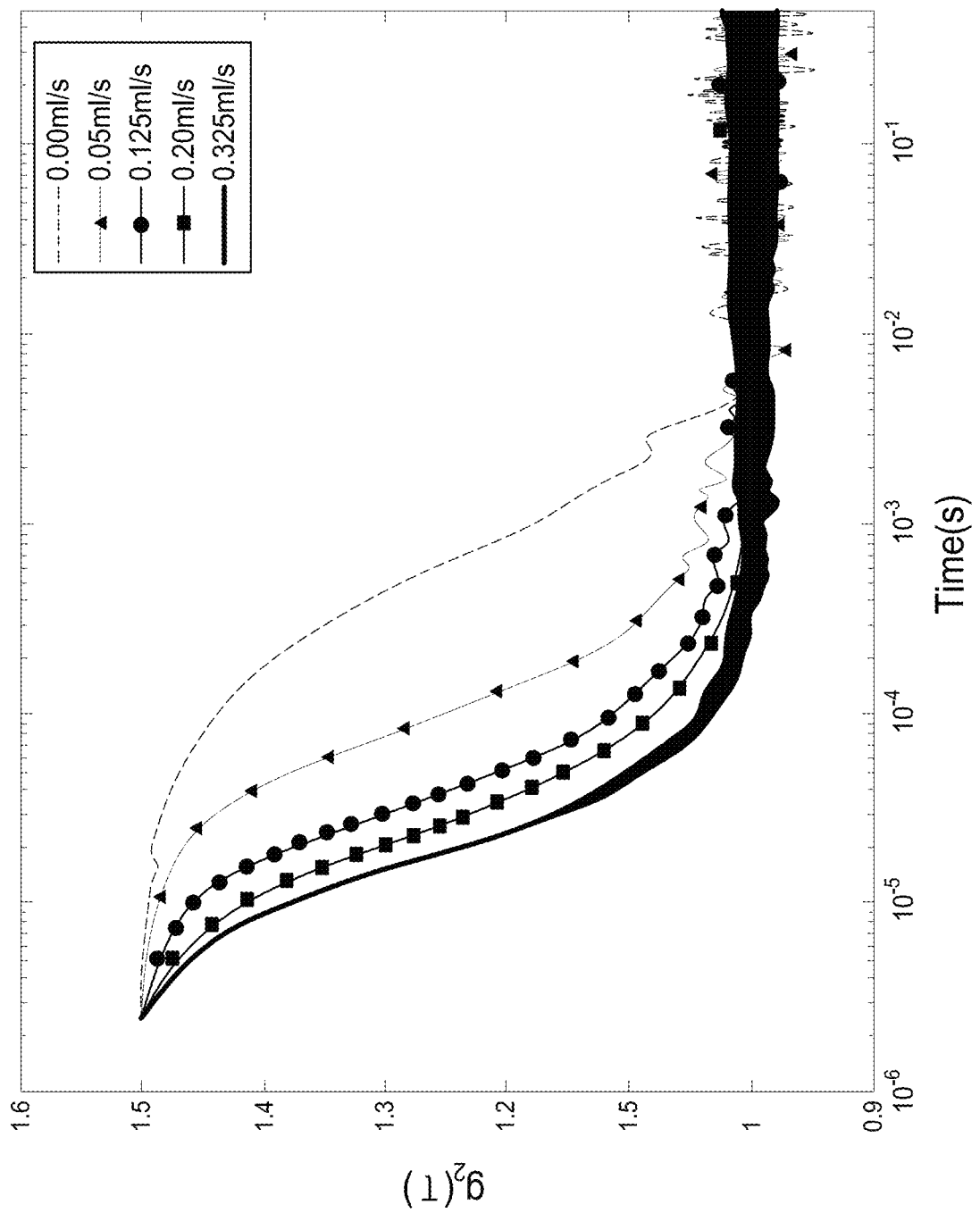
FIG. 4 is a graph of autocorrelation functions for different flow rates.

FIG. 3 is a schematic illustration of diffuse light penetration and detection in multi-layer tissue. As illustrated, a source 202 and a detector 204 are both positioned adjacent a portion of tissue 206. As noted above, in some embodiments optical fibers may be used to couple one or both of the source and detector to the tissue. The tissue 206 is multi-layer, including an upper layer 208 with no flow, and a deeper layer 210 with flow. A plurality of light-scattering particles 212 flow within capillaries in flow layer 210, and may include, for example, red blood cells. As light 214 is emitted from the source 202, it diffuses as it penetrates the tissue 206. As illustrated, a portion of the light 214 is diffused such that it is incident on the detector 204. The light 214 may follow a roughly crescent-shaped path from the source 202 to the detector 204. The depth of penetration of the light 214 detected by the detector 204 depends on the separation between the source and the detector. As the distance increases, penetration depth generally increases. In various embodiments, the separation distance may be between about 0.5 cm and about 10 cm, or in some embodiments between about 0.75 cm and about 5 cm. Preferably, in other embodiments the separation distance may be between about 1 cm and about 3 cm. In various embodiments, the separation distance may be less than about 10 cm, less than about 9 cm, less than about 8 cm, less than about 7 cm, less than about 6 cm, less than about 5 cm, less than about 4 cm, less than about 3 cm, less than about 2 cm, less than about 1 cm, less than about 0.9 cm, less than about 0.8 cm, less than about 0.7 cm, less than about 0.5 cm, less than about 0.4 cm, less than about 0.3 cm, less than about 0.2 cm, or less than about 0.1 cm. The penetration depth may vary, for example in some embodiments the penetration depth of the sensor may be between about 0.5 cm and about 5 cm, or in some embodiments between about 0.75 cm and about 3 cm. Preferably, in other embodiments the penetration depth may be between about 5 mm and about 1.5 cm. Of course, the tissue optical properties of the various layers also contribute to the penetration depth of the light, as does the intensity, wavelength, or other characteristics of the light source. These variations can allow for the depth of measurement to be adjusted based on the part of the body being analyzed, the particular patient, or other considerations. Measurements obtained by the detector 204 may then be processed and analyzed to calculate the autocorrelation function. As seen in FIG. 4, the autocorrelation function may be used to determine the flow rate in the tissue.

FIG. 4 is a graph of autocorrelation functions for different flow rates, with steeper decay of the autocorrelation curve indicating faster flow rates. The autocorrelation curves are plotted on a semi-logarithmic scale in the graph. As is generally known in the art, blood flow data can be analyzed by fitting each autocorrelation curve to a model, such a semi-infinite, multi-layer diffusion model. The fitted autocorrelation curves can then provide relative blood flow rates, which can be usefully applied during peripheral interventional procedures such as balloon angioplasty or surgery, or as a diagnostic tool.

Diffuse optical flow (DOF) sensors (which, as described above, can include either or both DCS and DSCA sensors) can be particularly useful in measuring microcirculation, for example in measuring blood perfusion in the foot. This technique can be additionally improved by employing the concept of pedal topography. One example of a topographical analysis of blood flow in the foot incorporates the concept of pedal angiosomes, as described above.

In many cases, prior to vascular intervention, an interventional radiologist or vascular surgeon will image the vasculature of interest, for example using fluoroscopy, computed tomography, ultrasound, or other imaging technique. With such imaging, several potential occlusions or lesions may be identified. Peripheral intervention, such as balloon angioplasty, atherectomy, or surgical bypass/grafts can be employed to re-open one or more of the identified occlusions or lesions ("the target lesions"), in an effort to restore perfusion to the affected region(s) of the foot. For these peripheral interventions to result in successful limb salvage, blood perfusion must reach a sufficient level that permits healing of the foot wound. Without a real-time perfusion monitor, a physician has no way of knowing for sure if an intervention has achieved an improvement in perfusion sufficient for wound healing, or at all. The use of real-time measurement of blood perfusion at various topographic locations of the foot, as described herein, addresses this problem. It provides objective quantitative perfusion data in real-time so that the physician can know with certainty whether a specific intervention at a target lesion has succeeded in restoring perfusion to the topographic region of the foot on which the wound is located. If a determination has been made that an acceptable level of perfusion at the desired topographic region has been achieved, the physician can avoid the additional risk associated with further intervention, and bring the procedure to a close. Alternatively, if a specific intervention at a target lesion has not resulted in any perfusion improvement as measured by a real-time perfusion monitor, the physician will thereby be guided to undertake the additional risk of proceeding onto secondary target lesions. The use of a real-time perfusion monitor thus averts the situation where a peripheral intervention procedure is ended prematurely prior to achieving the desired improvement in perfusion. It also guides physicians as to which target lesion (when revascularized) resulted in the greatest perfusion improvement at the desired topographic region of the foot. This real-time knowledge would in turn inform the physician as to the optimal placement for use of a drug-eluting balloon or other means to prolong the patency of the vessel in which the said lesion is located.

Figure 5A:
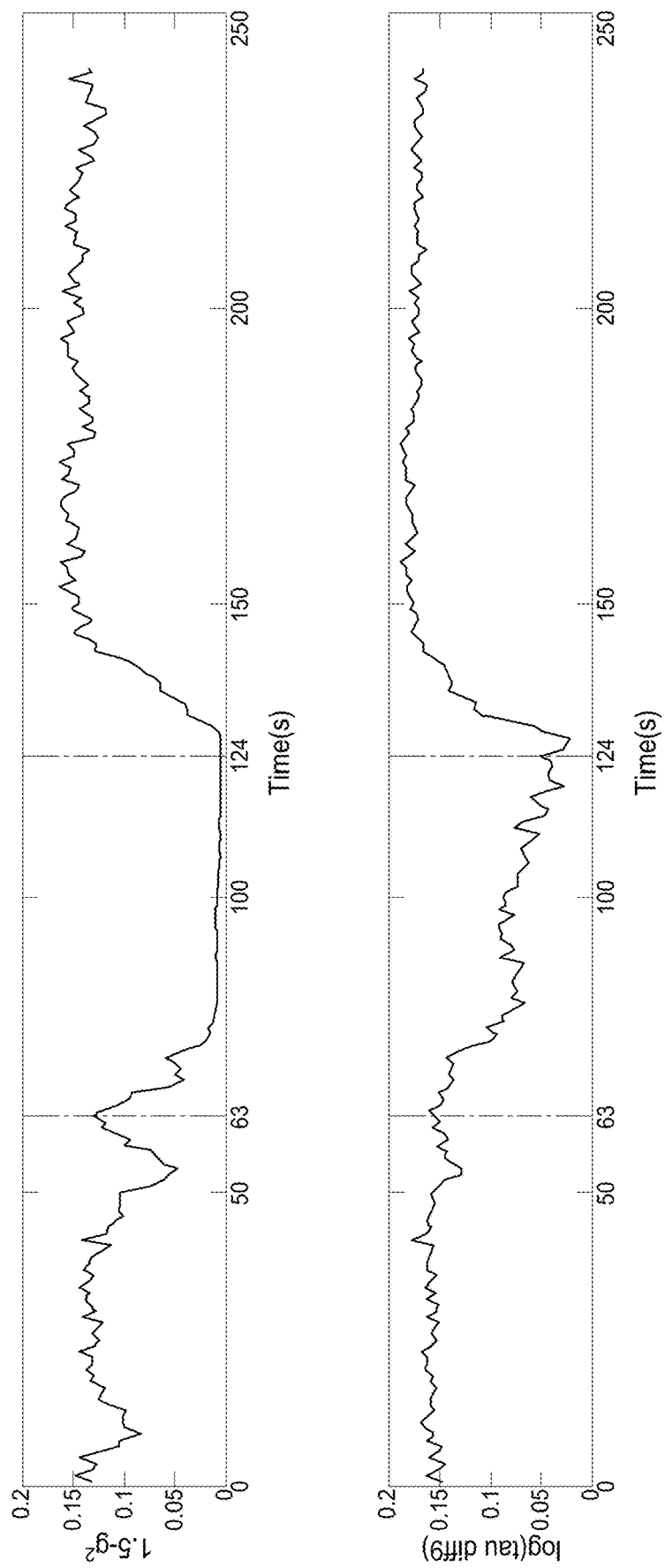
FIG. 5A is a graph of two blood flow indices (BFIs) during cuff occlusion protocol.
Figure 5B:
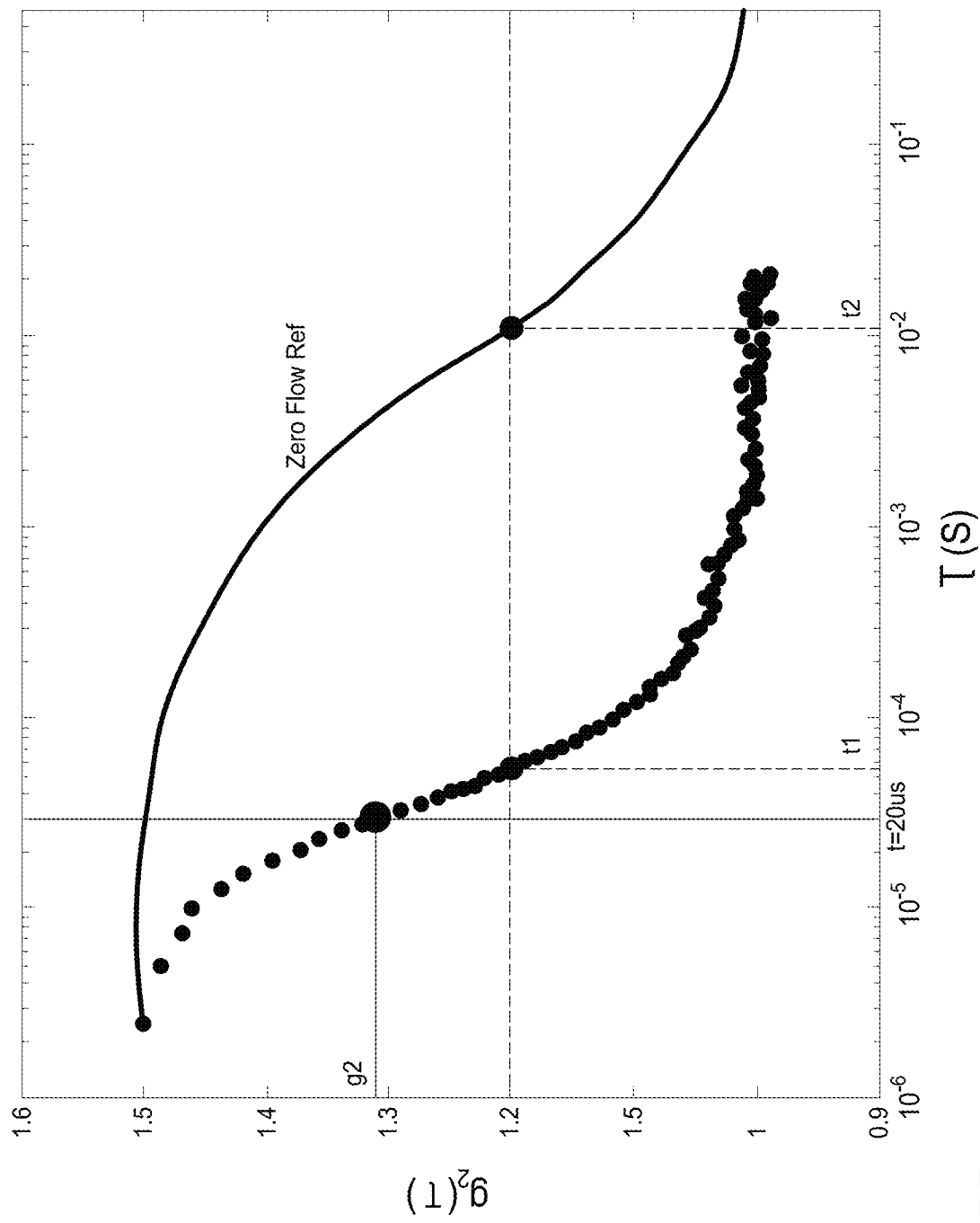
FIG. 5B is a graph of autocorrelation functions illustrating the derivation of the two BFIs of FIG. 5A.

Although changes in perfusion can be seen directly from the change in shape of the autocorrelation function, potentially more useful ways to define a blood flow index (BFI) have been developed. FIG. 5A is a graph of two such BFIs over time during a cuff occlusion protocol. The dashed vertical lines indicate the starting and stopping times of the cuff inflation. The top chart illustrates a BFI calculated from vertical crossing of the autocorrelation curve, while the lower chart illustrates a BFI calculated from horizontal crossing of the autocorrelation curve. FIG. 5B is a graph illustrating these two different methods of calculating BFI. The solid line represents the zero flow reference data, while the dotted line represents real-time autocorrelation data. The vertical crossing indicator compares the y-axis value ($g_2$) of the real-time autocorrelation data and the reference data at a given time. For example, the first indicator can be calculated as $1/g_2$ or $1.5-g_2$. The horizontal crossing indicator compares the time difference between the autocorrelation data and the reference data at a given flow rate. For example, the second indicator can be calculated as $\log(t2/t1)$.

Charts such as those shown in FIG. 5A, or other such indicia of blood flow, can be displayed to an operator in real-time via audible, visual, or tactile feedback. A physician may thereby be provided with substantially real-time feedback on the efficacy of a peripheral intervention. For example, during balloon angioplasty, a physician can monitor the BFI as measured on a specific location of the foot. The BFI will decrease while the balloon is inflated, and increase after deflation. After repeated inflation of the balloon to perform the angioplasty, the BFI should increase relative to the pre-angioplasty baseline, indicating that the angioplasty procedure has resulted in an improvement in perfusion at the target foot tissue. A BFI that does not increase relative to the pre-angioplasty baseline indicates that the balloon angioplasty was not successful in restoring perfusion. Providing such feedback in real-time is an enormous benefit to physicians performing vascular intervention. Rather than waiting post-operatively for hours or days to determine whether perfusion has been improved, during which time the foot may deteriorate to the point of requiring amputation, the use of DOF sensors at select pedal locations during the angioplasty procedure can provide immediate feedback, allowing the physician to continue, modify, or conclude the procedure as needed. As noted above, in various embodiments, the feedback may be provided within less than about 10 minutes, within less than about 5 minutes, within less than about 1 minute, within less than about 30 seconds, within less than about 10 seconds, or within less than about 1 second from measurement.

While the example above relates to balloon angioplasty, the use of DOF sensors to assess blood flow (whether relative, absolute, or both) in the foot can be advantageously applied before, during, or after a number of different interventions. For example, DOF sensors can be used to aid interventions such as rotational atherectomy, delivery of lytic substances, bypass procedures, or any other intervention.

Figure 6B:
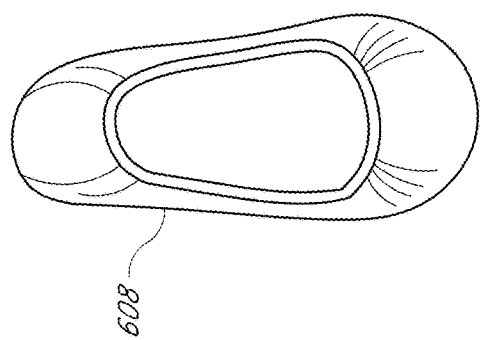
FIG. 6B illustrates a cover sock.
Figure 6C:
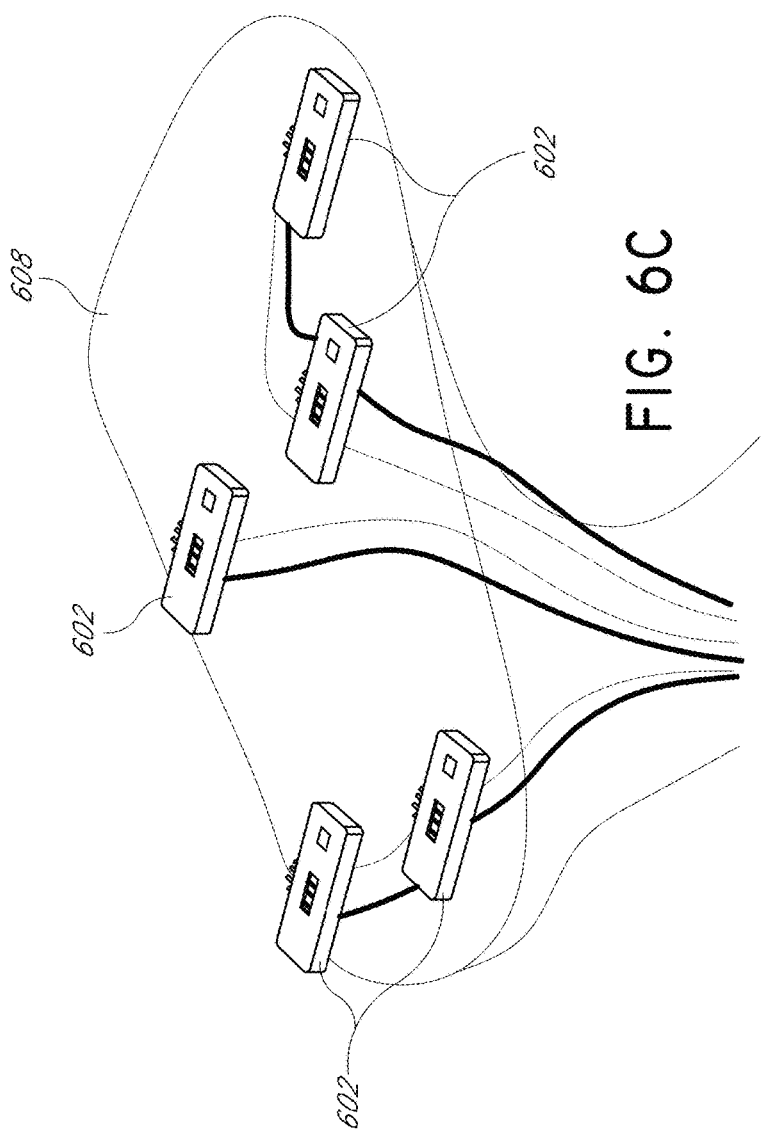
FIG. 6C illustrates a cover sock having a plurality of embedded side-firing DOF sensors.
Figure 6A:
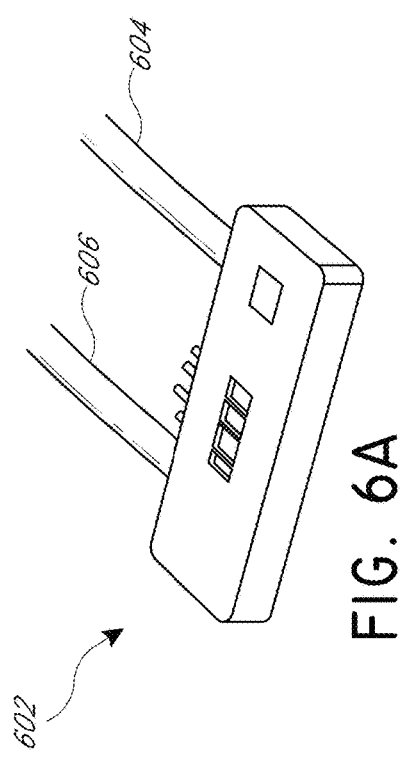
FIG. 6A is a schematic illustration of a side-firing DOF sensor.

As shown in FIGS. 1D-1H, DOF sensors can be separately placed at different topographical regions of the foot, for example the DOF sensors can be placed at each of the pedal angiosomes using separate support structures. In another embodiment, however, a plurality of DOF sensors can be incorporated into a single support structure for simultaneous measurement of different pedal regions, for example the pedal angiosomes. One such embodiment is illustrated in FIGS. 6A-6C. A side-firing DOF sensor is shown in FIG. 6A. As illustrated, light from a source can enter the sensor 602 through input cable 604, and can exit the sensor 602 through the output cable 606 towards the detector. In some embodiments, the input cable and the output cable can be bundled together. Rather than having the cable oriented perpendicular to the surface of the tissue to be measured, in this side-firing sensor the cable is oriented substantially parallel, with an internal prism, mirror, or other optical element redirecting light downwards towards the tissue. As a result, the DOF sensor 602 can be laid flat against the surface of the area to be measured, with the cables 604 and 606 extending substantially parallel to the surface. The overall effect is a more low-profile DOF sensor, with improved comfort, flexibility, and form-factor.

As used herein, the term "sensor" refers to the terminal end of the DOF system that makes contact with the sample, for example the patient's skin. The sensor may include an input optical fiber coupled to a source and an output optical fiber coupled to a detector. In other embodiments, the sensor may comprise receptacles configured to removably receive such optical fibers. The sensor defines the point at which input light is injected into the sample surface and the point at which scattered light is detected from the sample surface. In the illustrated embodiment, the DOF sensor 602 is substantially flat. However, in various embodiments, other shapes are possible. For example, the DOF sensor may be provided with a curved surface, for example contoured to correspond to contours of a patient's body. A DOF sensor may include a concave surface to correspond to the curvature of a wearer's plantar arch, for example. In some embodiments, the DOF sensor can be malleable to permit curvature and flexure to correspond to a patient's body. As noted above, the distance of separation between the source and the detector affects the penetration depth of measured light. More specifically, the significant distance is that between the position on the surface of the tissue at which light is injected, and position on the surface of the tissue at which light is detected. Accordingly, the side-firing DOF sensor 602 may be modified to provide for different penetration depths depending on the part of the body in which blood flow is to be measured. If the DOF sensor is adapted for use in measuring relatively deep blood flow, the source-detector separation can be greater than for a DOF sensor adapted for use in measuring relatively shallow blood flow. In some embodiments, this distance can be variable within an individual DOF sensor. For example, a mechanism may be provided allowing for the source input fiber and/or the detector output fiber to be moved along the length of the DOF sensor to modify the distance therebetween. For example, in some embodiments the source input fiber may be substantially fixed in relation to the sensor, while the detector output fiber is movable. Conversely, in some embodiments the detector output fiber can be substantially fixed in relation to the sensor, while the source input fiber can be movable. In some embodiments, the movable fiber can be slidable along the sensor, with a latch, screw, detent, or other structure provided to releasably fix the location of the movable fiber after a pre-selected distance has been set. In some embodiments, the movable fiber can be mounted onto a support that is threadably mated to a screw, such that rotation of the screw causes the support, and thereby the movable fiber, to be advanced closer to or further from the fixed fiber. Various other configurations are possible. In other embodiments, various optical components within the interior of the DOF sensor can be provided to alter the effective source-detector distance. For example, the positions of the fibers may be fixed, while internal prisms or mirrors or other optical components can be adjusted to direct the light (incident light from the source or scattered light to the detector) to or from different locations.

FIG. 6B illustrates, as one example of a support structure, a cover sock 608 designed to slip over the patient's foot. As shown in FIG. 6C, a plurality of side-firing DOF sensors 602 can be carried by a cover sock. In some embodiments, the side-firing DOF sensors 602 are arranged at positions corresponding to different pedal angiosomes. Since each DOF sensor 602 can be made thin and flexible, they can be sewn or otherwise attached to the cover sock 608 at the appropriate positions. The optical fibers can be bundled and guided outside the foot covering 608 and connected to an analyzer. With this design, applying the multiple DOF sensors to a patient's foot can be quick and essentially foolproof, which is particularly advantageous in the hectic environment of an operating room or catheter lab.

Figure 6D:
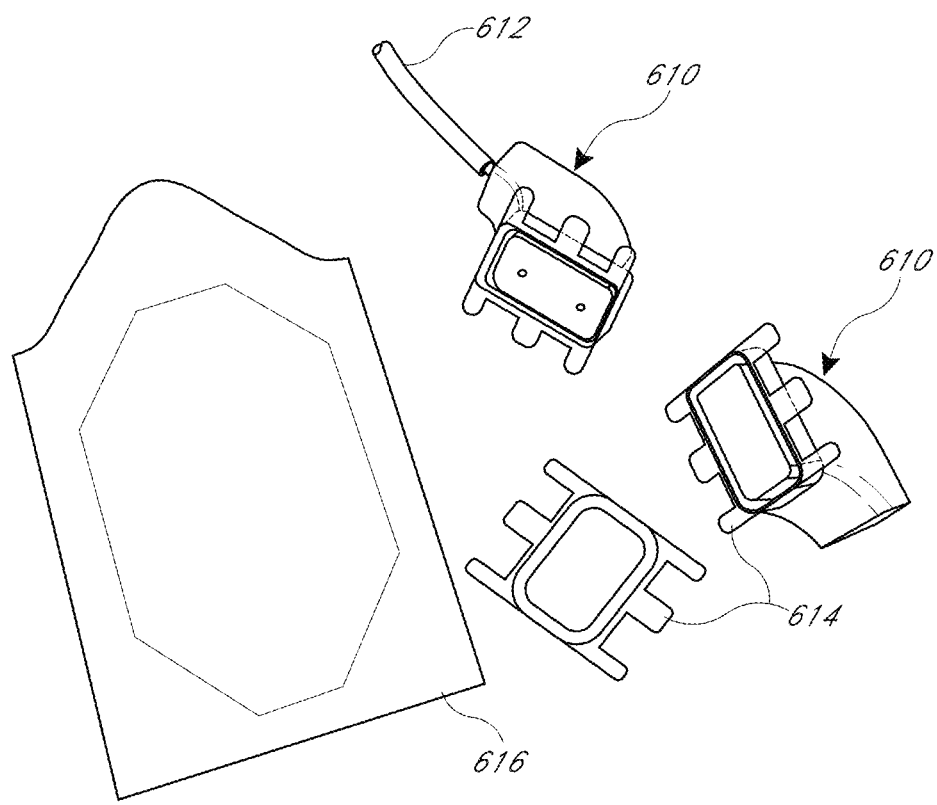
FIG. 6D illustrates another embodiment of a DOF sensor, with a retention ring and adhesive material.
Figure 6E:
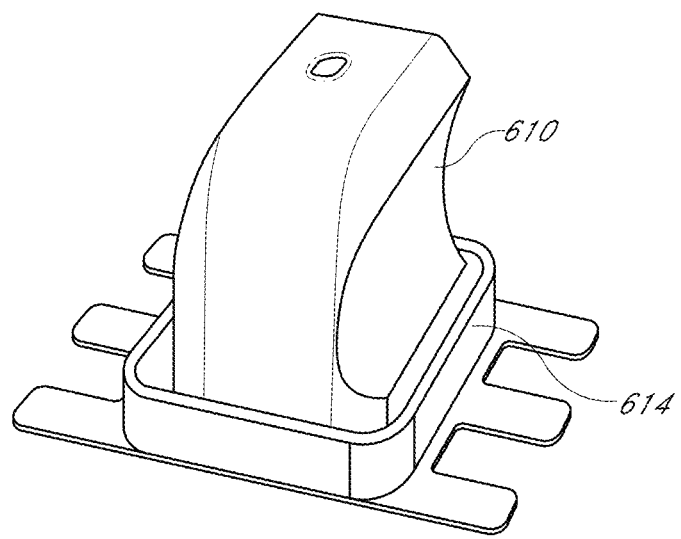
FIG. 6E illustrates a detail view of the DOF sensor head shown in FIG. 6D.

FIGS. 6D and 6E illustrates another example of a support structure and DOF sensor. As illustrated, the DOF sensor 610 includes bundled wires 612 extending therefrom. The bundled wires 612 include both the input and output optical fibers, as described above. A retention ring 614 is configured to surround the bottom-facing edge of the DOF sensor 610. The retention ring 614 can be affixed to a surface (e.g., a patient's skin) via adhesive pads 616. The adhesive pads 616 can take a variety of forms, including, for example Tegaderm™ Film. In other embodiments, adhesive material is deposited onto the retention rings without the use of separate adhesive pads.

As illustrated, the retention ring 614 can define an aperture configured to receive the DOF sensor 610 therein. In various embodiments, the retention ring 614 can include one or more retention elements configured to releasably mate with corresponding retention elements on the DOF sensor 610. The engagement of corresponding retention elements thereby releasably locks the sensor 610 into position with respect to the retention ring 614. In various embodiments, a latch, screw, detent, or other structure can be provided to releasably fix the DOF sensor 610 to the retention ring 614.

Various other support structures are possible. For example, in some embodiments the DOF sensors may be carried by a series of straps configured to be wrapped around a patient's foot so as to position the DOF sensors appropriately with respect to the desired measurement regions of the pedal topography, for example different pedal angiosomes. In some embodiments, the DOF sensors may be carried by a sheet of flexible material to be wrapped around the patient's foot. In some embodiments, the support structure may be configured to carry one, two, three, four, five, or more DOF sensors. In some embodiments, two or more support structures may be provided for a single patient. For example a first support structure may carry two DOF sensors and be positioned over a first portion of a patient's foot, while a second support structure may carry two additional DOF sensors and be positioned over a second portion of the patient's foot. In various embodiments, the support structure may be wearable, for example it may be a garment such as a cover sock, shoe, etc. In some embodiments, the support structure can include a strap or series of straps. In other embodiments, the support structure can comprise an adhesive material by which one or more DOF sensors can be attached to a patient's skin. For example, in some embodiments, each of the DOF sensors can be provided with an adhesive on the tissue-facing side so as to ensure that the sensors contact the skin. In some embodiments, mechanical pressure can be applied to the DOF sensors to ensure that they are pressed against the skin—for example an external wrap may be used, or the elasticity of a cover sock or other foot covering may itself be sufficient to ensure that the DOF sensors are adequately held against the skin. In some embodiments, DOF sensors can be embedded into a foot plate sensor such as those used by podiatrists. An individual may step onto the foot plate, and one or more DOF sensors carried by the foot plate can measure absolute and/or relative blood flow at various locations on the foot.

In some embodiments, each DOF sensor may be carried by a different support structure. In other embodiments, a support structure can be configured to carry any number of DOF sensors, for example two, three, four, five, or more. In various embodiments, the support structure can be configured such that, when the support structure is positioned over a patient's foot, the position of the DOF sensors correspond to different topographical locations in the foot including selected pedal angiosomes. The support structure can be configured to carry DOF sensors corresponding to any combination of topographical locations in the foot including pedal angiosomes. For example, in one embodiment a support structure may be configured to carry DOF sensors adapted to measure blood flow at the calcaneal branch of the posterior tibial artery and at the calcaneal branch of the peroneal artery. In another embodiment a support structure can be configured to carry DOF sensors adapted to measure blood flow at the medial plantar artery, the lateral plantar artery, and the calcaneal branch of the posterior tibial artery. Various other configurations are possible, such that the support structure can be tailored to provide DOF sensors at the desired measurement locations.

Figure 7:
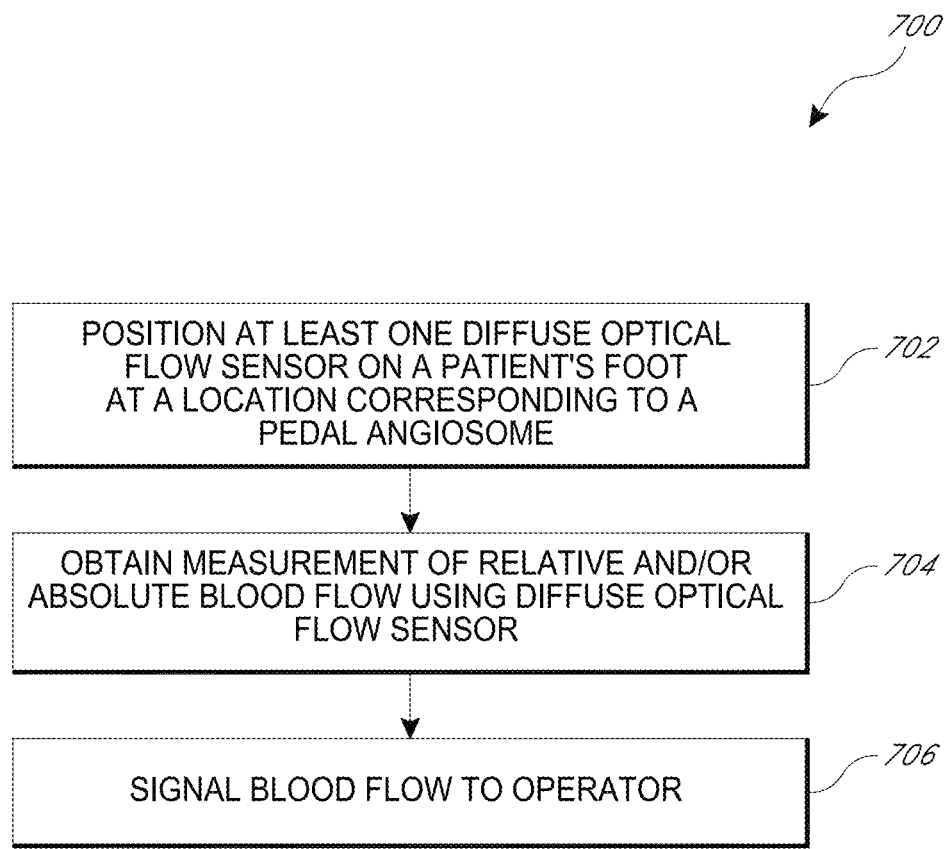
FIG. 7 is a flow diagram of a method for analyzing absolute and/or relative blood flow.

FIG. 7 is a flow diagram of a method for analyzing relative blood flow. The process 700 begins in block 702 with positioning at least one DOF sensor on a patient's foot at a location corresponding to a pedal angiosome. As noted above, in some embodiments a plurality of such DOF sensors may be positioned at various places on a patient's foot, or other places on the patient's body. In some embodiments, a plurality of such DOF sensors can be used to obtain simultaneous measurements from different topographical locations in the foot including different angiosomes. The process 700 continues in block 704 with obtaining measurement of absolute and/or relative blood flow using the DOF sensor. As noted above, DOF techniques can provide an autocorrelation function indicative of the absolute and/or relative blood flow within the tissue. The process 700 continues in block 706 with signaling the absolute and/or relative blood flow to the operator. For example the signal may be provided via visual, audible, or tactile communication. In some embodiments, the absolute and/or relative blood flow can be signaled to the operator in substantially real-time, for example within 1 second of measurement. In some embodiments, a display may be provided that shows the autocorrelation functions, a chart of blood flow indices (BFIs), or other indicator of the absolute and/or relative blood flow. Such a display can provide the operator with real-time feedback to guide intra-operative decision-making.

As described above, sensor head designs for DOF sensors traditionally employ fibers with either metal or ceramic ferrules to protect the fiber tip, hence the typical sensor head design is limited to a vertical contact scheme where light out of the fiber is directly coupled into a sample. The vertical fiber design suffers from a number of disadvantages when used in applications for blood perfusion monitoring: it adds bulk, height and positional instability to the sensor head; it may require additional means of support to achieve stable and consistent contact with the skin; and for these reasons, it may cause patient discomfort after prolonged application.

Therefore, it is advantageous to implement a low profile horizontal contact sensor head that is both simple and cost-effective. FIGS. 8A-8C illustrate an embodiment of such a DOF sensor head. FIG. 8A illustrates a schematic cross-section of the sensor head 800, and FIGS. 8B and 8C illustrate plan views of two possible embodiments for the sensor head 800. As illustrated, a support structure includes a receptacle member 804 with a groove to receive the optical fibers 806 therein, and a reflector member 808 with a reflecting surface. As illustrated, optical fibers 806 are applied horizontally onto the surface of the sample 810, and part of the fiber body is disposed within a groove in a receptacle member 806, and the distal tip of the fiber 806 configured to be positioned between the surface of sample 810 and a reflecting surface of the reflector member 808. Light coming out of the source fiber tip will be reflected off of the reflecting surface in this gap and will be directed towards the sample 810. For the detector fiber, the reverse will happen: only those light paths that fall within the acceptance cone will be reflected off of the reflecting surface and collected by the fiber. In some embodiments, the reflecting surface may comprise a sheet of aluminum foil mounted onto a compliant backing such as a rubber, silicone, or foam pad. It will be appreciated that a wide range of materials may be utilized as reflectors including metal foils, metal films, optically reflective coatings, interference gratings, nanostructured meta-materials, or any other material with suitable optical properties.

When applied to a sample, the planar DOF sensor places the fiber in optical communication with the sample. In some embodiments an optically transparent sterile barrier comprising at least one optically transparent layer may be disposed between the fiber and the sample. The at least one optically transparent layer may be configured to have adhesive coatings to facilitate attachment of the planar DOF sensor onto the surface of the sample/tissue. For example, surgical tape may comprise a support configured to receive the DOF sensor thereon, and to couple the DOF sensor to the sample.

Figure 9B:
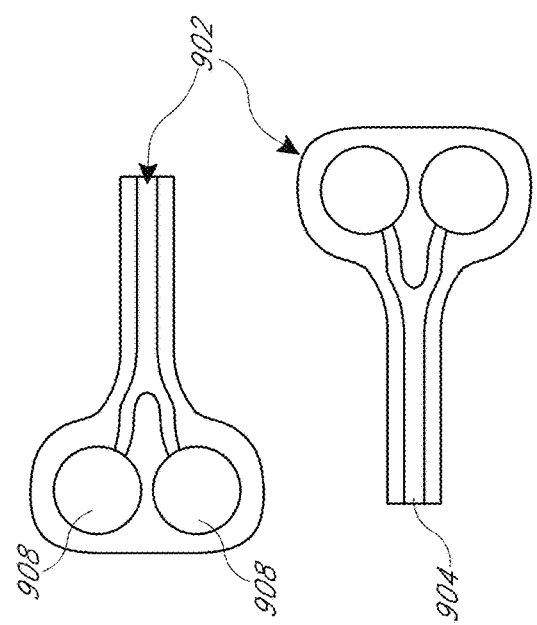
FIGS. 9A-9D illustrate another embodiment of a DOF sensor with a horizontal sensor head.
Figure 9A:
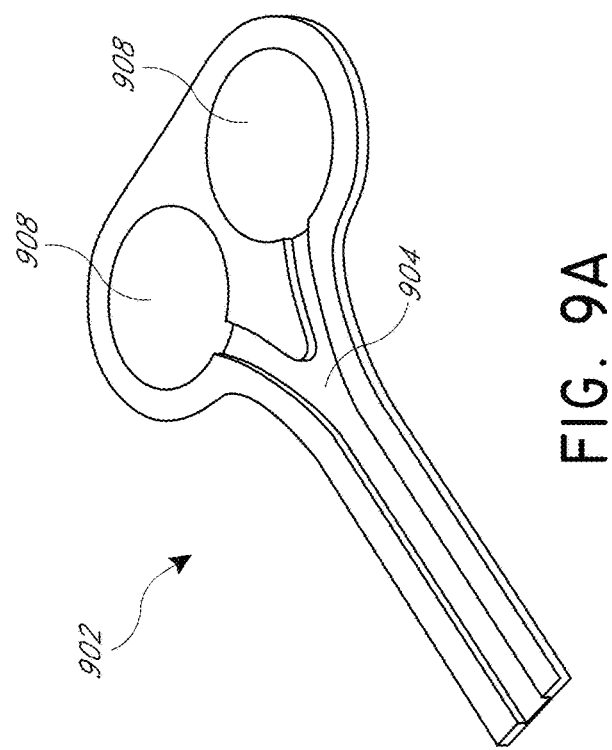
Figure 9C:
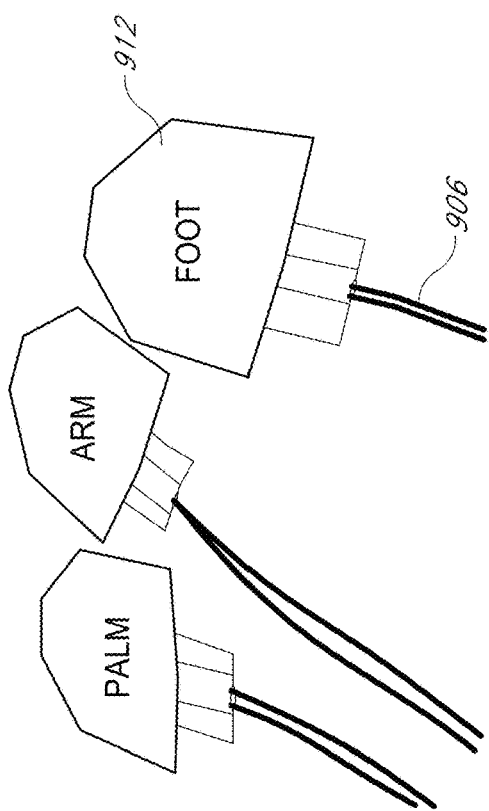
Figure 9D:
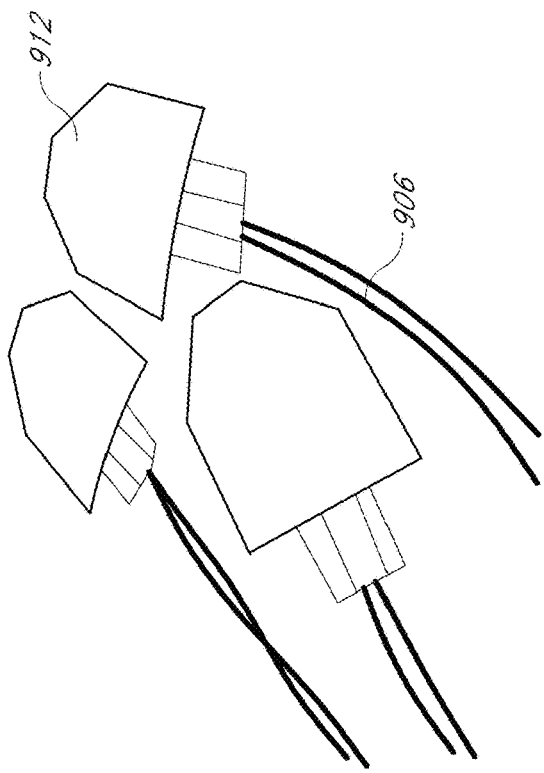

FIGS. 9A-9D show one embodiment of the supports fabricated using 3D printing, with a support comprising an adhesive layer that is disposed between the patient/tissue and the optical fibers. FIGS. 9A and 9B illustrate the support member 902, with 9C and 9D showing top and bottom views, respectively, of the sensor heads 900 prepared with a layer of surgical adhesive tape 912 to be disposed between the patient's skin and the fibers. In FIGS. 9C and 9D, the reflector pads 908 and tips of fibers 906 are obscured by the adhesive liner of the surgical tape 912. In other embodiments, the at least one optically transparent layer may not have an adhesive coating, whereupon the planar DOF sensor may be attached to the sample by the application of surgical tape, a mechanical clamp, adjustable strap, or other means.

Figure 10:
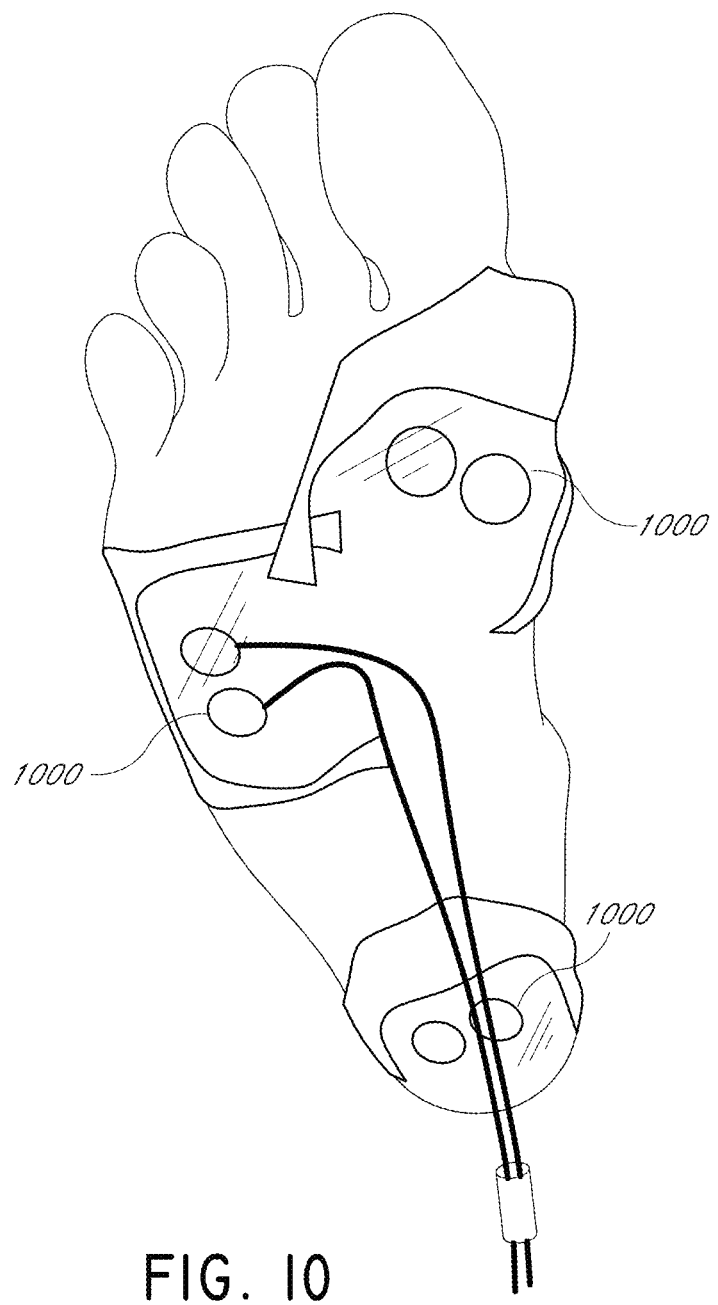
FIG. 10 illustrates a DOF sensor attached to a patient's foot.
Figure 11:
FIG. 11 illustrates a DOF sensor attached to a patient's hand.

FIG. 10 illustrates a plurality of DOF sensors 1000 attached to a patient's foot. With a source-detector separation of approximately 1.5 cm on a healthy human foot, arterial cuff occlusion protocol observations display typical blood perfusion variations—i.e., a sudden decrease and plateauing during occlusion, and sharp overshoot and subsequent recovery to baseline value after release of the cuff pressure. FIG. 11 illustrates a DOF sensor attached to a patient's hand. The computer screen indicates a decrease in blood perfusion during arterial cuff occlusion and subsequent reactive hyperemia, indicating healthy blood flow in the hand. In the illustrated graph, two sets of cuff-occlusion are shown with two distinct peaks of reactive hyperemia.

Advantages of the planar DOF sensor head include its low weight, its stability during prolonged application, and a higher level of patient comfort. Its performance is not compromised compared to a vertical sensor head design, and it can be utilized in any optical transmission measurement system in semi-infinite geometry.

Although some embodiments described above refer to applying DOF sensors to determining absolute and relative blood flow in the foot, other applications are possible. For example, in some embodiments, DOF sensors can be used to assess blood flow in plastic and reconstructive surgical flaps. In some embodiments, DOF sensors can be used to assess blood flow in the hand. In some embodiments, the DOF sensors can be positioned within the body, for example within natural orifices, to assess blood flow. In various such embodiments, DOF sensors can be disposed in accordance with angiosome theory.

Although this application has been disclosed in the context of certain embodiments and examples, it will be understood by those skilled in the art that the present application extends beyond the specifically disclosed embodiments to other alternative embodiments and/or uses of the application and obvious modifications and equivalents thereof. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present application herein disclosed should not be limited by the particular disclosed embodiments described above.

What is claimed is:

1. A system for assessment of peripheral blood flow characteristics in deep tissue, the system comprising:
   a support structure configured to be positioned onto an external body part of a patient;
   at least one diffuse optical flow (DOF) sensor carried by the support structure and configured to be positioned in optical communication with a skin surface of the patient, the at least one DOF sensor comprising a return optical conduit, and at least one input optical fiber comprising an end configured to be positioned proximate the skin surface of the patient, the at least one input optical fiber in optical communication with a coherent laser light source;
   a photodetector operably connected to the at least one DOF sensor; and
   a processor configured to analyze data from the at least one DOF sensor to determine blood flow characteristics at a location near the at least one DOF sensor when the support structure is positioned onto the external body part of the patient, the processor configured to determine blood flow characteristics in blood vessels of the patient by determining a spatial speckle contrast ratio ($K_s$) or a temporal speckle contrast ratio ($K_t$) and determining $1/K_s^2$ or $1/K_t^2$ from intensity fluctuations, and correlating $1/K_s^2$ or $1/K_t^2$ values with blood flow; wherein the at least one DOF sensor is configured to capture light scattered diffusively into tissue and transmitted at a depth of penetration of between 5 mm and 50 mm.

2. The system of claim 1, wherein the support structure comprises a retention ring and an adhesive material.

3. The system of claim 1, wherein the support structure comprises a strap having the at least one DOF sensor attached thereto.

4. The system of claim 1, wherein the support structure comprises surgical tape.

5. The system of claim 1, wherein the at least one DOF sensor comprises a plurality of DOF sensors, wherein the plurality of DOF sensors are arranged such that when the support structure is positioned onto the patient's external body part, at least two of the DOF sensors are over different topographical locations relating to different angiosomes of the patient.

6. The system of claim 5, wherein the plurality of DOF sensors comprise at least four DOF sensors, wherein the at least four DOF sensors are arranged such that when the support structure is positioned over the patient's external body part, wherein the at least four DOF sensors are over different topographical locations relating to different angiosomes of the patient.

7. The system of claim 1, wherein the processor is configured to provide feedback indicative of the blood flow characteristics to the display in real-time.

8. The system of claim 1, wherein the processor is configured to provide feedback indicative of the blood flow characteristics within 10 seconds from measurement.

9. A method for assessment of peripheral blood flow characteristics, the method comprising:
   disposing at least one diffuse optical flow (DOF) sensor proximate a skin surface of a patient in optical communication with a first location on the patient, the at least one DOF sensor comprising a return optical conduit;
   transmitting light from a coherent laser light source through at least one input optical fiber of the at least one DOF sensor, the at least one input optical fiber comprising an end positioned proximate a second location on the patient;
   obtaining measurements at the first location of intensity fluctuation from a depth of penetration of between 5mm and 50mm within the patient's microcirculatory channels from the at least one DOF sensor;

analyzing the measurements obtained from the first location via a processor to determine blood flow characteristics, wherein analyzing comprises determining the spatial speckle contrast ratio ($K_s$) or the temporal speckle contrast ratio ($K_t$) and determining $1/K_s^2$ or $1/K_t^2$ from the intensity fluctuations, and correlating $1/K_s^2$ or $1/K_t^2$ values with blood flow; and signaling the determined blood flow characteristics to an operator.

10. The method of claim 9, wherein disposing the at least one DOF sensor comprises placing a support structure onto the foot of the patient, the at least one DOF sensor being carried by the support structure.

11. The method of claim 9, wherein disposing at least one DOF sensor comprises disposing a plurality of DOF sensors at a respective plurality of locations on the foot of the patient.

12. The method of claim 11, wherein the plurality of locations comprises at least two locations corresponding to different topographical locations in the foot including different pedal angiosomes.

13. The method of claim 12, wherein the plurality of locations comprises at least four locations corresponding to four different topographical locations in the foot including different pedal angiosomes.

14. The method of claim 9, wherein the signaling comprises providing visual, audible, or tactile indicia of the determined blood flow characteristics.

15. A method for assessment of peripheral blood flow characteristics, the method comprising:

disposing a plurality of diffuse optical flow (DOF) sensors each comprising a return optical conduit at a respective plurality of locations in optical communication with a skin surface of a patient, wherein at least two of the plurality of locations correspond to different topographical locations in the patient including different angiosomes;

transmitting light from a coherent laser light source through at least one input optical fiber of each of the plurality of DOF sensors, each of the at least one input optical fibers comprising an end positioned proximate the skin surface of the patient;

determining blood flow characteristics at each of the plurality of locations in the extremity of the patient via a processor by analyzing detected scattered coherent light at from depth of penetration of between 5 mm and 50 mm from within the patient's microcirculatory channels, wherein analyzing comprises determining the spatial speckle contrast ratio ($K_s$) or a temporal speckle contrast ratio ($K_t$) and determining $1/K_s^2$ or $1/K_{t1}^2$ from intensity fluctuations, and correlating $1/K_s^2$ or $1/K_t^2$ values with blood flow; and signaling the determined blood flow characteristics to an operator.

* * * * *